(12) United States Patent
Tworkoski et al.

(10) Patent No.: US 7,635,663 B2
(45) Date of Patent: Dec. 22, 2009

(54) METHOD FOR THINNING FRUIT BLOSSOMS USING EUGENOL

(75) Inventors: Thomas Tworkoski, Middletown, MD (US); Stephen Miller, Martinsburg, WV (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/801,622

(22) Filed: May 10, 2007

(65) Prior Publication Data

US 2007/0270313 A1  Nov. 22, 2007

Related U.S. Application Data

(60) Provisional application No. 60/801,454, filed on May 18, 2006.

(51) Int. Cl.
*A01N 31/02* (2006.01)
*A01N 41/00* (2006.01)

(52) U.S. Cl. .................................................. 504/162
(58) Field of Classification Search .............. 504/116.1, 504/162
See application file for complete search history.

(56) References Cited

U.S. PATENT DOCUMENTS

| 4,009,020 A | 2/1977 | Starke et al. |
| 4,374,661 A | 2/1983 | Fritz et al. |
| 5,118,340 A | 6/1992 | Butselaar et al. |
| 5,242,891 A | 9/1993 | Larsen et al. |
| 6,440,901 B1 | 8/2002 | Long |
| 2001/0039246 A1 | 11/2001 | Duan et al. |
| 2002/0193250 A1 | 12/2002 | Bessette |

OTHER PUBLICATIONS

International Patent Application No. PCT/US07/69006, May 16, 2007, (Priority Date May 18, 2006).
Dennis Jr., F., "The History of Fruit Thinning", *Plant Growth Regulation*, vol. 31, 2000, pp. 1-16.
Southwick, S., et al., "Controlling Cropping in 'Loadel' Cling Peach Using Gibberellin: Effects on Flower Density, Fruit Distribution, Fruit Firmness, Fruit Thinning, and Yield", *J. Amer. Soc. Hort. Sci.*, vol. 120, (6), 1995, pp. 1087-1095.
Myers, S., et al., "Partial Flower Thinning Increases Shoot Growth, Fruit Size, and Subsequent Flower Formation of Peach", *HortScience*, vol. 37, (4), 2002, pp. 647-650.
Tworkoski, T., "Herbicide Effects of Essential Oils", *Weed Science*, vol. 50, 2002, pp. 425-431.
Wertheim, S., "Developments in the Chemical Thinning of Apple and Pear", *Plant Growth Regulation*, vol. 31, 2000, pp. 85-100.

*Primary Examiner*—Johann R Richter
*Assistant Examiner*—Danielle Sullivan
(74) *Attorney, Agent, or Firm*—John D. Fado; G. Byron Stover (57) ABSTRACT

A method for thinning fruit blossoms involving applying an effective amount of a blossom thinning composition to the blossoms and associated living tissue (e.g., nearby buds and leaves) of fruit bearing plants (e.g., fruit trees), the blossom thinning composition comprising eugenol as an active ingredient for the purpose of blossom thinning.

17 Claims, 7 Drawing Sheets
(6 of 7 Drawing Sheet(s) Filed in Color)

Eugenol

METHOD FOR THINNING FRUIT BLOSSOMS USING EUGENOL

REFERENCE TO RELATED APPLICATION

This application claims the benefit of U.S. Provisional Application No. 60/801,454, filed 18 May 2006, which is incorporated herein by reference in its entirety.

BACKGROUND OF THE INVENTION

The present invention relates to a method for thinning fruit blossoms involving applying an effective amount of a blossom thinning composition to the blossoms and associated living tissue (e.g., nearby buds and leaves) of fruit bearing plants (e.g., fruit tree), the blossom thinning composition comprising eugenol as an active ingredient for the purpose of blossom thinning.

Peach and apple trees produce heavy crop loads that require thinning to ensure that the fruit will achieve marketable size and that flower bloom is not inhibited the following year (Wertheim, S. J., Plant Growth Regulation, 31: 85-100 (2000)). Removing 50% of peach flowers has been shown to increase average size of the remaining fruit and increase overall crop value (Myers, S. C., et al., HortScience, 37: 647-650 (2002)). Growers can spend $1730 per ha to hand-remove excess blossoms and this expense translates to annual costs of over $156,000,000 in the U.S. Chemical thinning of peach flowers reduced the estimated costs of hand thinning up to 310 per ha (Southwick, S. M., et al., J. Amer. Soc. Hort. Sci., 120: 1087-1095 (1995)). Buds, blossoms, and fruit are removed by hand or with chemicals, but few chemical thinners are available and those available are not always effective (Costa, G., et al., Rivista di Furtticoltura e di Ortofloricoltura, 66: 48-54 (2004)). There is a need for new chemical thinners, especially environmentally-friendly thinners, to replace the costly, labor-intensive hand thinning that is currently used by growers (Dennis, F. G., Plant Growth Regulation, 31: 1-16 (2000)).

Figure 1:
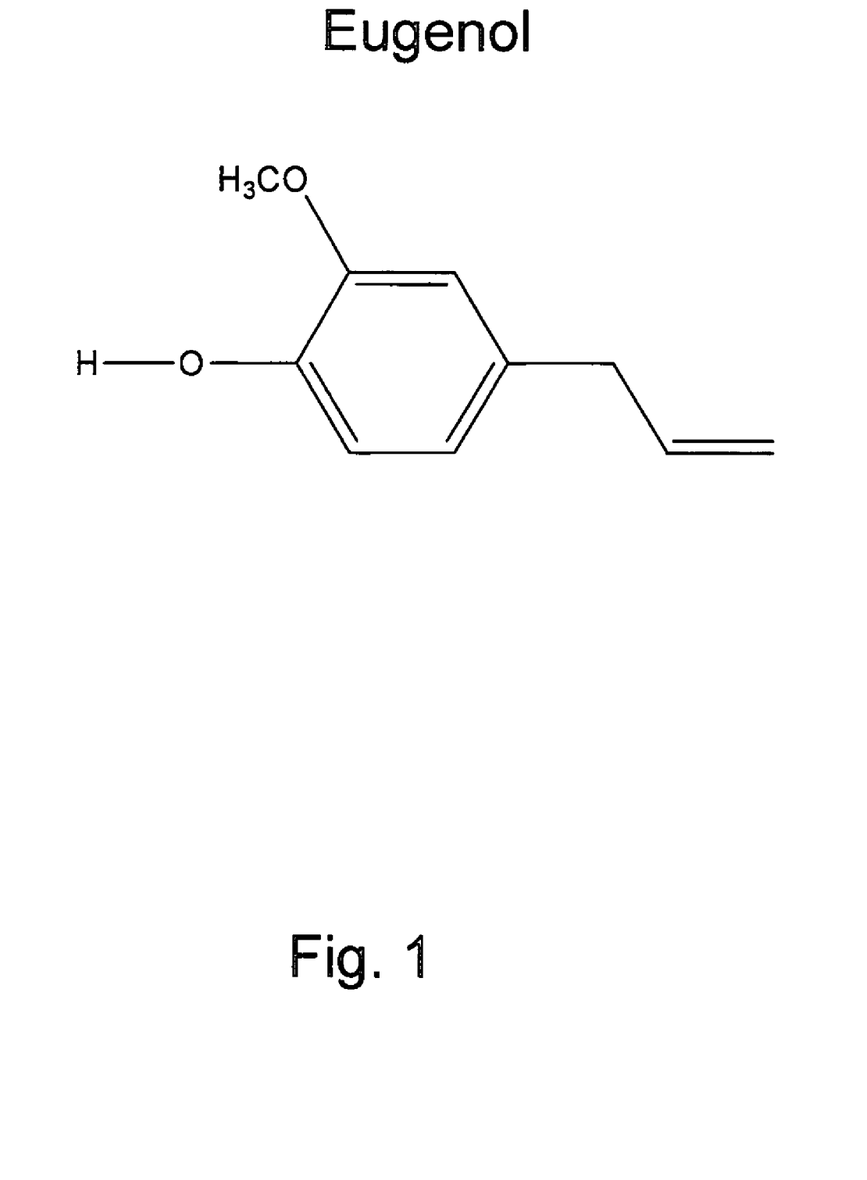
FIG. 1 shows the chemical structure of eugenol.

We have found that eugenol (2-methoxy-4-(2-propenyl) phenol; FIG. 1) acts as a blossom thinner in fruit trees (e.g., peach, apple, pear).

SUMMARY OF THE INVENTION

In accordance with the present invention, there is provided a method for thinning fruit blossoms involving applying an effective amount of a blossom thinning composition to the blossoms and associated living tissue of fruit bearing plants, the blossom thinning composition comprising eugenol as an active ingredient for the purpose of blossom thinning.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

DETAILED DESCRIPTION OF THE INVENTION

The invention provides a process for thinning fruit blossoms. The process of the invention includes applying an effective amount of a blossom thinning composition to the blossoms and associated living tissue (e.g., nearby buds and leaves) of a fruit bearing plant (e.g., fruit tree), the blossom thinning composition including eugenol (2-methoxy-4-(2-propenyl)phenol; FIG. 1). Generally, the blossom thinning composition comprises eugenol suspended in water. Other compounds (e.g., adjuvants) may be added to the composition provided they do not substantially interfere with the intended activity of the composition; whether or not a compound interferes with blossom thinning activity can be readily determined by one skilled in the art, for example, by the procedures utilized below.

The eugenol may be from any source, for example naturally-derived eugenol extracted from cinnamon (*Cinnamomum zeylanicum*) or clove (*Syzgium aromaticum*). Essential oils containing eugenol are generally regarded as safe and can be applied directly to food crops without extensive EPA review. In addition, essential oils are natural products and therefore are likely to be accepted by organic growers.

The method of the present invention is useful for blossom thinning of fruit trees (e.g., peach, apple, pear) to produce a reduced number of larger, more marketable fruit from each tree and at the same time minimize fruit losses due to breaking of tree branches in harsh weather.

The method of the present invention may be applied to fruit trees which have reached at least about 10% blossom (e.g., 10% blossom; 100% blossom is the point in time when all blossoms have just opened; thus, 10% blossom is the point in time when one-tenth of the blossoms on a particular tree have opened). If less than about 50% (e.g., less than 50%) of the blossoms are open when the first application is made, it is likely that one or two additional applications would be required for optimum thinning. The fruit thinning process is generally carried out after at least about 10% (e.g., at least 10%) of the blossoms on a tree are fully opened up until up to about 2 to about 3 weeks (e.g., 2-3 weeks) after 100% of the blossoms have opened. Preferably the fruit thinning process is carried out at any point after about 50% blossom and up to about 100% blossom (e.g., 50-100% blossom). The optimum time to thin a fruit tree will depend upon several factors including the type of fruit, the cultivar, the climatic conditions, and the type and amount of thinning agent being applied. For some fruit or cultivar species, the best thinning effects may be accomplished before the trees reach 100% blossom whereas for others it may be best to wait until several days after 100% blossom has been reached.

The method of the present invention is generally carried out by the application of an effective amount of eugenol to fruit trees to thereby produce a reduction in the number of blossoms and consequently produce a reduction in the number of fruit, as well as an increase in the size of the fruit produced. Eugenol is preferably applied in the form of a suspension in a concentration of about 1.5 to about 6% (e.g., 1.5-6%) and more preferably from about 2 to about 4% (e.g., 2-4%) (% based on the concentration of active ingredient (eugenol) in water on a volume (v/v) basis). The optimal eugenol concentration will likely depend on flower density, tree size, and air temperatures; an optimal concentration of eugenol in water would be close to 3% for peach and apple. The lower limit is generally determined by the upper limit on application volume for the particular application equipment being employed, as well as by the type of fruit being thinned. The upper concentration limit will generally be dictated by phytotoxicity considerations as higher concentrations of eugenol have a localized phytotoxic effect on the trees. Thus, a concentration should be selected which provides adequate fruit thinning without unwanted phytotoxic effects on the remainder of the tree. The attached examples show that such concentrations can be selected by routine experimentation with the particular species of fruit to be thinned.

The eugenol is generally applied in a manner similar to the manner in which commercial insecticides are applied. More particularly, conventional equipment such as knapsack sprayers, hand held spray guns, mist blowers, and aerial spraying equipment among others may be used. The composition is applied the same way as in pesticide application. Preferably an airblast sprayer is utilized that enables uniform coverage of blossoms.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Materials and methods: Initial work determined general foliar and blossom injury response to increasing rates of eugenol in apple and peach trees. Eugenol was prepared as a suspension in water and applied with a hand-held sprayer (Sure Shot, Milwaukee Sprayer Mfg. Co., Inc., Milwaukee, Wis.) to flowers to the point of drip. Spray was applied to peach trees (*Prunus persica* L. 'Redhaven' on Lovell rootstock) at 60 psi when air temperature was approximately 21° C. with sunny conditions. Naturally-derived eugenol, extracted from cinnamon (*Cinnamomum zeylanicum*) or clove (*Syzgium aromaticum*), was obtained from Citrus and Allied (Floral Park, N.Y.). Peach tree flowers were approximately 60% in bloom when eugenol was applied on 14 Apr. 2003. One tree received one application of each concentration of eugenol. One-hundred flowers per tree, uniformly distributed throughout the crown were selected for measurement 24 hr, 1 mo, and 2 mos after application. At 24 hr, flowers with wilted pistils and stamens were considered killed and nonviable. Surviving fruit were counted 1 and 2 mo after application. Peaches were harvested on 7 Aug. 2003 from each treated tree. Total fruit number and weight and size of individual fruit were measured.

Eugenol was applied to apple trees (*Malus domestica* 'Ace Spur Red Delicious' on M.7 rootstock) on 23 Apr. 2003 when "king" blossoms had been fully opened and subtending flowers were just opening. Temperatures were 18° C. under partly sunny conditions. One-hundred five-cluster groups of flowers were evaluated for damage 24 hr after application. Surviving fruit from the original clusters were counted 1 and 2 mo after application. Apples were harvested on 17 Sep. 2003 from each treated tree. Total fruit number and weight and size of individual fruit were measured.

Figure 2:
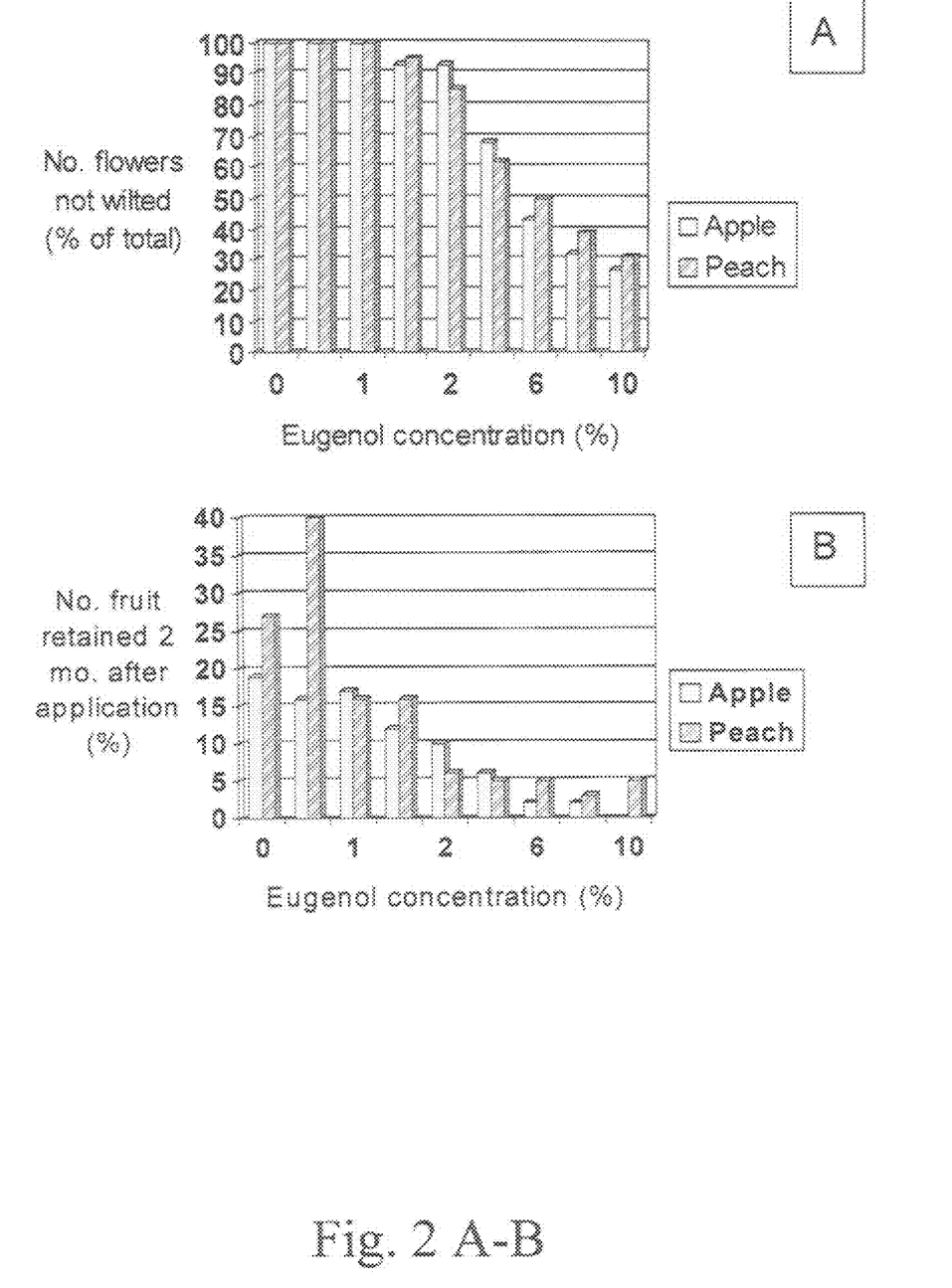
FIG. 2 shows the effect of increasing eugenol concentrations on % flowers not wilted at 24 h after application (A) and on % fruit retained at 2 mo after application (B) in 2003.
Figure 3A:
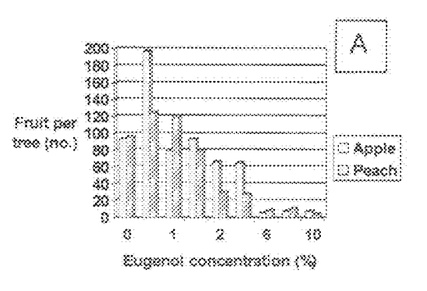
FIG. 3 shows the effect of increasing eugenol concentrations on fruit number and weight (kg) per tree (A and B, respectively), on average fruit weight (g) (C) and on % distribution of peach fruit by diameter size class distribution (D) in 2003.
Figure 3B:
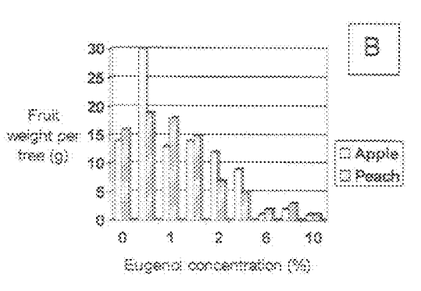
Figure 3C:
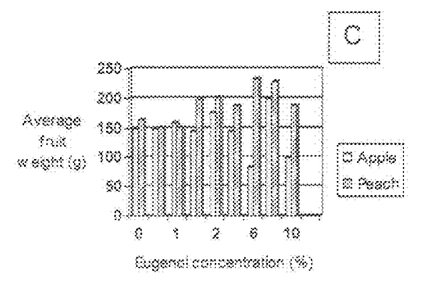
Figure 3D:
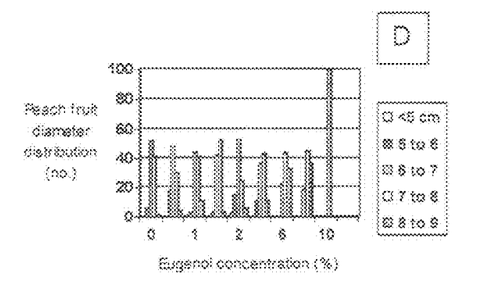

Results and discussion: Within 1 hr of application of essential oil, peach flowers began to appear bleached and leaf tips developed necrotic lesions. Injury was apparent at 1.5% and increased proportionately as concentrations increased to 10%, which had notable injury (FIG. 2). Little injury on peach flowers was observed at concentrations below 1.5%. By 2 mo after application, little injury could be observed on peach trees treated at the highest concentration, 10%, but few fruit remained on the tree at this concentration. The effective rate for flower thinning and fruit retention was between approximately 1.5 and 6% essential oil (Table 1, FIG. 3). No fruit or leaf injury was seen on 12 Jun. 2003 at 6% concentration.

As with peach flowers, apple flower injury was apparent at 1.5% eugenol and injury increased with increasing concentrations up to 10% essential oil (FIG. 2). By 2 mo. after application, little injury was observed at the highest concentration and no fruit or leaf injury was observed on 12 Jun. 2003 at the 6% concentration. As with peach trees, the effective rate for flower thinning and fruit retention appeared to occur between approximately 1.5 and 6% essential oil (Table 1, FIG. 2).

The total number and weight of peaches and apples per tree began to decrease at concentrations of essential oil at approximately 1.5 and 2% (FIG. 3). Average fruit weight generally was higher in thinned peach trees (FIG. 3). The proportion of peaches and apples in the larger size classes increased in trees thinned with essential oil (FIG. 3). However, fruit load was excessively reduced at some higher concentrations.

Figure 4:
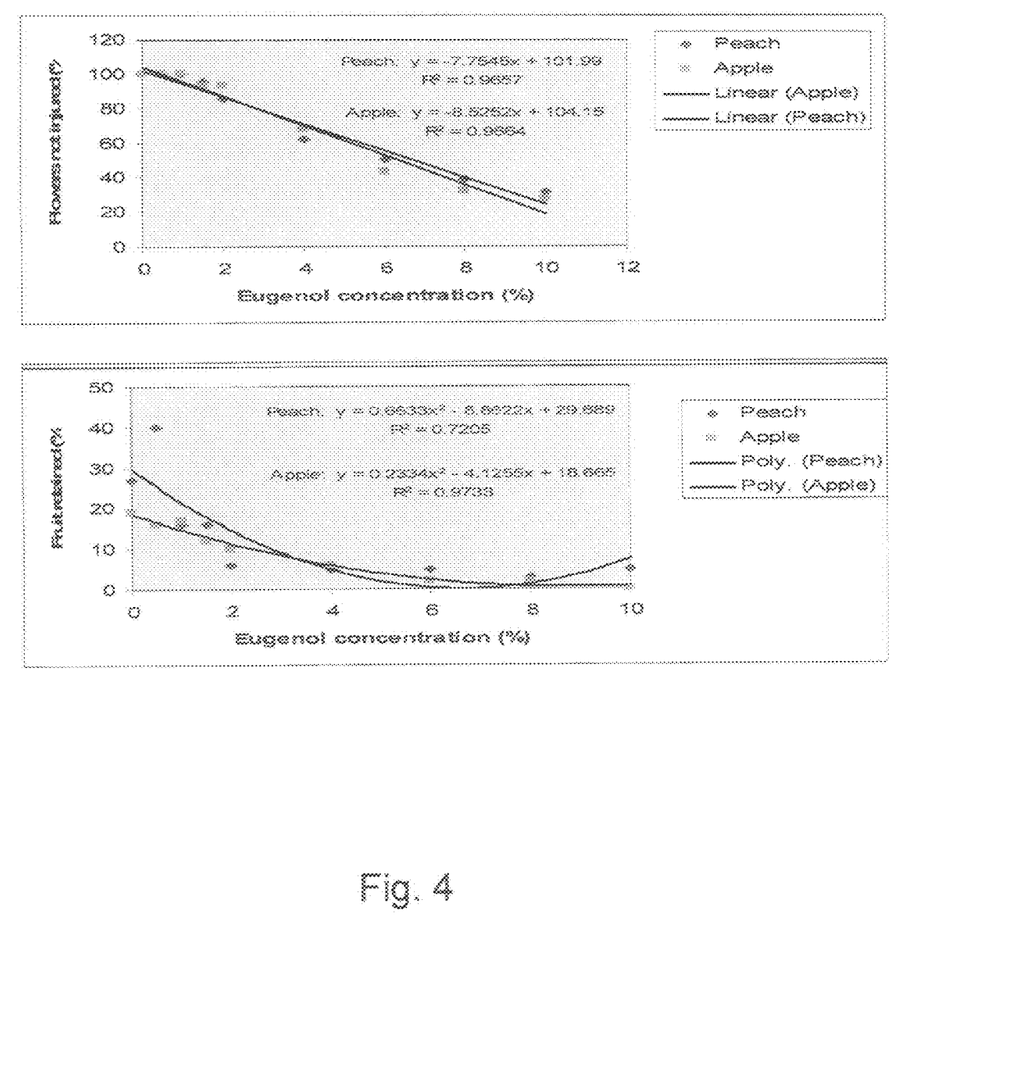
FIG. 4 shows the effects of increasing rates of eugenol application on flowers not injured 24 hr after application (top) and on fruit retention 2 months after application (bottom) of peach and apple trees in 2003.

FIG. 4 shows the effects of increasing rates of eugenol application on flowers not injured 24 hr after application (top) and on fruit retention 2 months after application (bottom) of peach and apple trees in 2003.

Results from 2003 surprisingly demonstrated that eugenol was an effective blossom thinner in peach and apple trees and that the degree of thinning was responsive to rate of eugenol applied. Furthermore, initial injury to leaves was surprisingly short-lived as no sign of eugenol-induced phytotoxicity was seen by 2 months after application. However, results also demonstrated a clear need for uniformity of eugenol spray as variability of thinning within a crown was estimated to be associated with uneven application. In 2004, a new eugenol-based herbicide, Matran® EC, was used along with eugenol to evaluate the effects of a commercial formulation on uniformity of spray and thinning; two non-eugenol thinners that have similar blossom burn back effects were also included for comparison (results discussed below).

In 2004, fewer concentrations of eugenol were tested in comparison with other chemical blossom thinners in apple and peach. Eugenol (Citrus & Allied) and a naturally-derived, eugenol-based herbicide, Matran® (EcoSMART Technologies, Inc., Franklin, Tenn.; active ingredients are clove oil (50%) and other ingredients (50%; wintergreen oil, butyl lactate, and lecithin)) were applied to peach and apple trees. 'Redhaven' on Lovell peach received treatment on 19 Apr. 2004 with a pressurized power mist blower back pack sprayer. Peach trees had been planted in April 1997 with a 3-m spacing between trees. Treatments included eugenol and Matran® each applied at 1, 2, 4, and 8%. Additional chemical thinners were Wilthin® (monocarbamide dihydrogen sulphate; D-88; EPA Registration Number 06889100004; Unocal Corporation, Los Angeles, Calif.), applied at 3.2 gal/100 gal and ammonium thiosulfate (ATS) (Amthio; Allied Chemical Company, Houston, Tex.) applied at 5.25 gal/A. Untreated controls and hand-thinned trees were included for comparison. Each tree was an experimental unit, buffer trees surrounded each treated tree, and there were 5 replications arranged in a completely randomized design.

Two apple cultivars in separate blocks were used as experimental apple trees. 'Bisbee Spur Delicious' on MM.111 were planted in 1987 with a tree spacing of 12.5 ft and row spacing of 16 feet (218 trees/A). 'Acespur Delicious' on Mark were planted in 1989 with tree spacing of 6 feet and 14 feet between rows (341 trees/A). Eugenol (0, 2, 4, and 6%) and ATS (3.5 gal/A) were applied to 'Bisbee' on 21 Apr. 2004 and Matran® (0, 2, 4, and 6%) was applied to 'Acespur' on 22 Apr. 2004 with a pressurized power mist blower back pack sprayer. Each tree was an experimental unit, surrounded by buffer trees, with 4 single tree replications arranged in a completely randomized design.

Response variables included (1) percent flowers wilted 24 hr after application based on a 100 flower (peach) or flower cluster (apple) sample per tree; (2) number apple fruit retained after June drop from the same 100-flower sample per tree; (3) number and weight of fruit per tree at harvest by size category; (4) visual estimation from two people of foliar and shoot damage. Four branches per tree, each with 25 flowers, were measured; two branches opposite each other were perpendicular to the drive alley and the other two branches were opposite each other and parallel to the drive alley.

Figure 5:
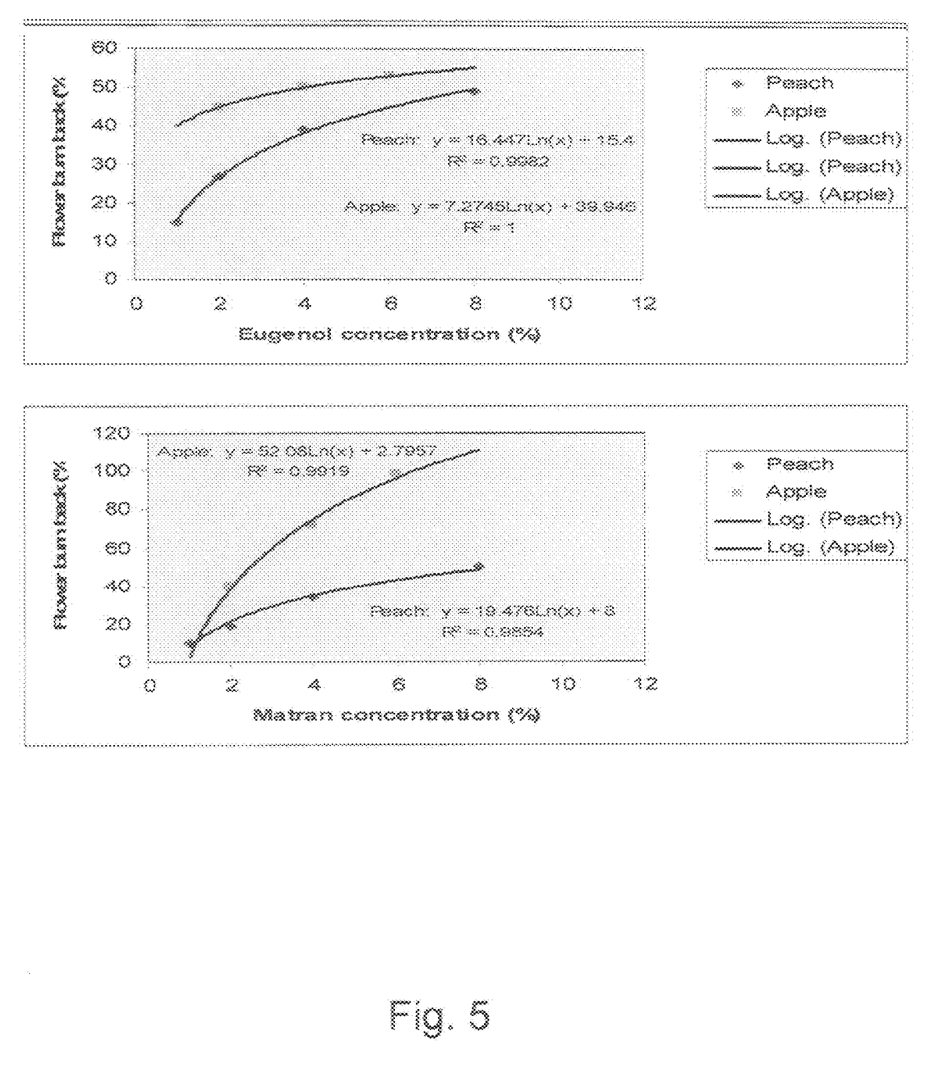
FIG. 5 shows the effects of increasing rates of eugenol (top) and Matran® (bottom) application on flower burn back of peach and apple in 2004.

Results and discussion: The amount of flower burn back in a peach tree was related to dose of eugenol and Matran® (Table 2); FIG. 5 shows the effects of increasing rates of eugenol (top) and Matran (bottom) application on flower burn back of peach and apple trees in 2004. Reliable flower burn back occurred at 4 to 8% eugenol and Matran®. Flower burn back was similar between 8% eugenol, 8% Matran®, and ATS (approximately 50% burn back). However, there was still significant variation in injury to flowers within a tree, likely due to nonuniform coverage with flower thinners. This variation was reflected in the lack of statistical difference between flower burn back estimates for eugenol concentrations of 2 and 4% (27 and 49% burn back, respectively). The variation was somewhat less with Matran® treatments, which may reflect an effective suspension of eugenol in the formulation of Matran®.

Figure 6:
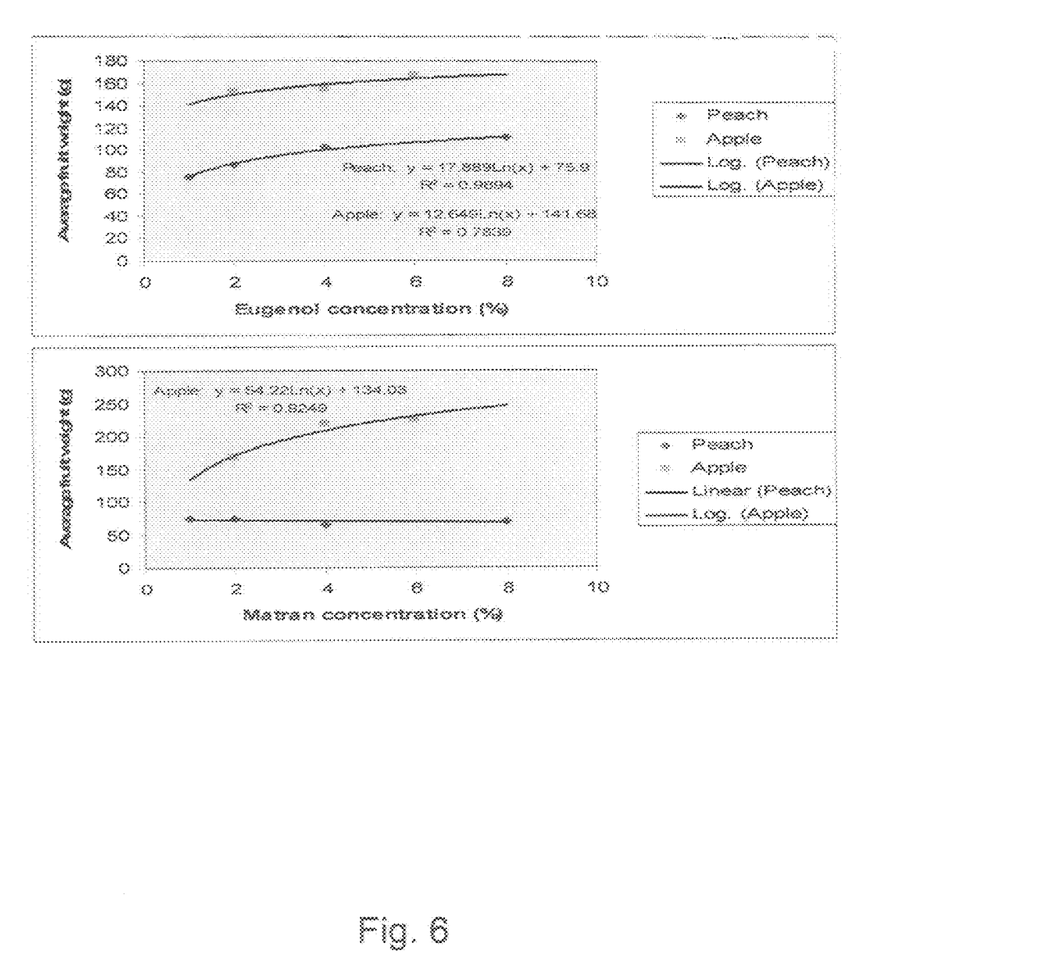
FIG. 6 shows the effects of increasing rates of eugenol (top) and Matran® (bottom) application on average fruit weight at harvest of peach and apple in 2004.

Fruit number per peach tree was reduced by Wilthin®, ATS, and hand-thinning compared with control (Table 3); FIG. 6 shows the effects of increasing rates of eugenol (top) and Matran (bottom) application on average fruit weight at harvest of peach and apple trees in 2004. Eugenol reduced fruit number when applied at rates higher than 2%. Average weight per fruit was highest in trees that were thinned with ATS, Wilthin®, eugenol (4 and 8%), and by hand-thinning (Table 3). Thinning with ATS resulted in the largest increase of fruit in the larger size classes (Table 4). These thinning treatments were most successful in reducing fruit load and providing economically-desirable fruit size.

In apple trees, eugenol caused significant flower burn back (Table 2). The number of apples was reduced by eugenol, but not significantly, possibly due to nonuniform cover at time of application (Table 3). Matran® provided good flower burn back and fruit thinning in June compared with control. Eugenol and ATS did not affect yield (Table 3). Matran® at 4 and 6% reduced number but not weight of fruit per tree. Spearman Correlation Coefficient of number of flowers injured the day after thinner application and number of fruit retained on the same tree in June was −0.65 ($P>F=0.001$; n=35). This correlation indicated that estimates of flower injury served as a good index of fruit retention at the end of the season.

In apple, lack of uniform eugenol coverage of flowers affected burn back. Trees that were first sprayed with a particular concentration of eugenol showed much more flower burn back than trees that were sprayed last; particularly noticeable with the 6% eugenol rate. Apple flowers were particularly susceptible to eugenol and concentrations of 2 to 4% gave good blossom thinning. Matran® at 2 to 6% was a reasonable working range in apple. Some apple blossoms opened seven days after spray (28 Apr. 2004), indicating that some "surviving" apples were due to later development.

In 2005, research focused on applying chemical thinners to apple trees using an airblast sprayer (Durand-Wayland, LaGrange, Ga.) to ensure uniform chemical coverage throughout the tree canopy. On Apr. 26, 2005 three thinning agents were applied to 'Gala' on M.26 apple trees (planted in November 1997) in full blossom. The three thinning agents were ATS, Matran®, and eugenol, all applied at 2, 4, or 6%. ATS is now used by growers as a foliar fertilizer that also functions as an unregistered thinner. However, ATS can be inconsistent and often provides unsatisfactory blossom thinning. Treatments were arranged in 4-tree plots and there were 4 blocks containing all 8 treatments. Data was collected from 2 trees per plot, so each treatment was an average of 8 trees. Data was analyzed by analysis of variance and Duncan's Multiple Range Test.

Figure 7:
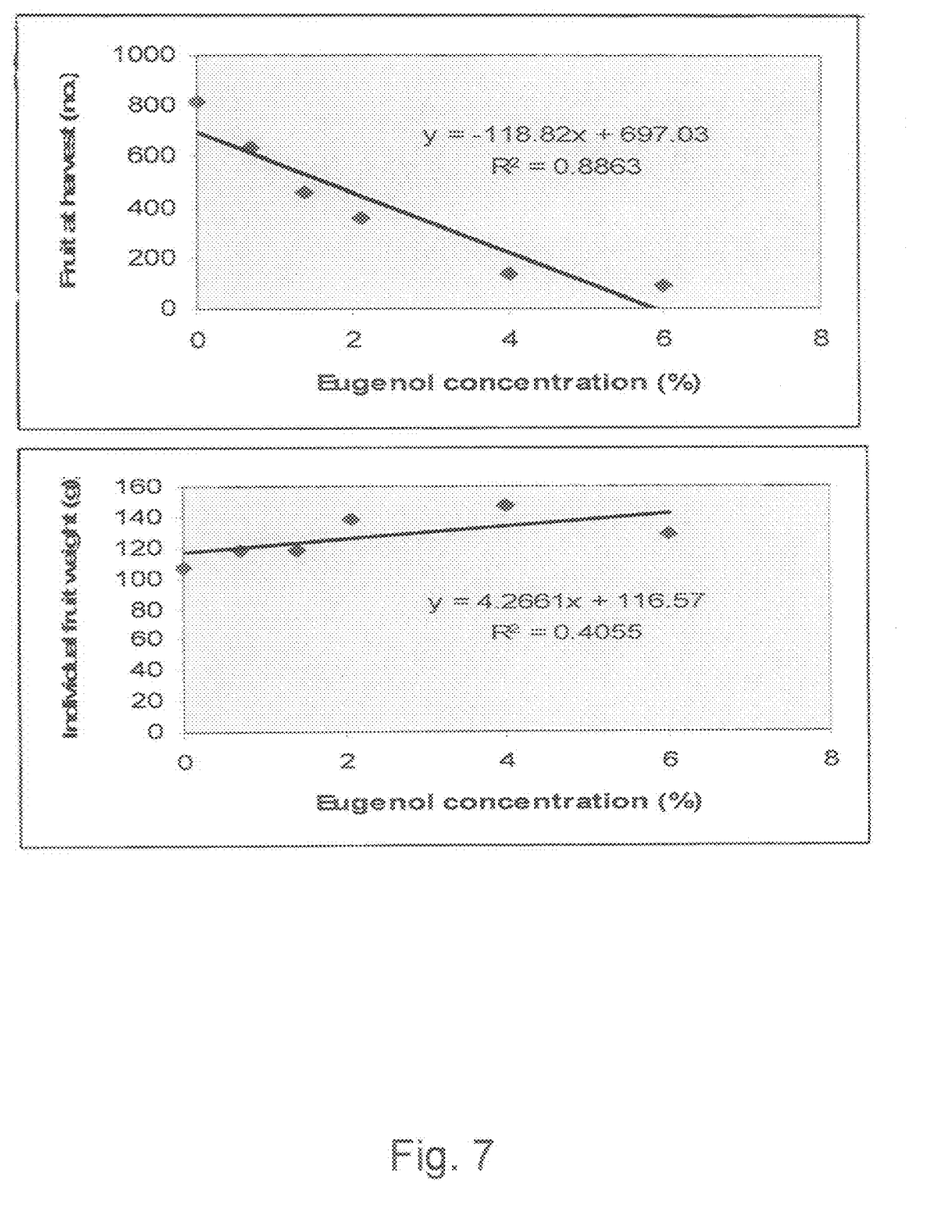
FIG. 7 shows the effects of increasing rates of eugenol, when applied as eugenol alone or in the Matran® formulation on number of fruit (top) and on average fruit weight (bottom) at harvest of apple in 2005.

The speed sprayer used to apply thinning agents in 2005 appeared to give uniform coverage that was not obtained with the backpack mist blower sprayer used in 2004. In 2005, ATS was not a good thinner (Table 4); FIG. 7 shows the effects of increasing rates of eugenol when applied as eugenol alone or in the Matran formulation on number of fruit (top) and on average fruit weight (bottom) at harvest of apple in 2005. The "organically-acceptable" herbicide Matran® was applied at 2, 4, and 6% concentrations and a blossom thinning dose-response was observed (Table 4). Matran® contains 34% clove oil and eugenol is the active ingredient of clove oil. Eugenol alone was applied at 4 and 6% and a blossom thinning dose response also was observed (Table 4). There was a clear dose response of fruit number and weight to eugenol. Optimal concentrations likely are between 2 and 4%. With a spray technology that gave uniform blossom coverage, a very clear thinning was observed with increased concentrations of eugenol, verifying the controllability and efficacy of this compound. Leaves were injured by eugenol as the blossoms were treated but this injury was superficial, did not persist, and was not observed within four weeks of application.

All of the references cited herein are incorporated by reference in their entirety. Also incorporated by reference in their entirety are the following references: Tworkoski, T., Weed Science, 50: 425-431 (2002); U.S. Patent Application Publication 2001/00392246. Also incorporated by reference in their entirety are the following U.S. Pat. Nos. 6,440,901; 5,118,340; 4,009,020.

Thus, in view of the above, the present invention concerns (in part) the following:

A method for thinning fruit blossoms, said method comprising (or consisting essentially of or consisting of) applying an effective amount of a blossom thinning composition to the blossoms (and associated living tissue) of fruit bearing plants, said blossom thinning composition comprising (or consisting essentially of or consisting of) eugenol as an active ingredient for the purpose of blossom thinning.

The above method, wherein said eugenol is applied in the form of an aqueous suspension having a concentration of eugenol from about 1.5 to about 8% (e.g., 1.5-8%) or from about 1.5 to about 6% (e.g., 1.5-6%) or from about 2 to about 4% (e.g., 2-4%) or about 3% (e.g., 3%).

The above method, wherein said fruit bearing plants are fruit trees. The above method, wherein said fruit trees are apple trees, peach trees, or pear trees. The above method, wherein said fruit trees are apple trees. The above method, wherein said fruit trees are peach trees.

The above method, wherein said blossom thinning composition is applied to said blossoms of fruit bearing plants when said fruit bearing plants are at about 10% blossom up to about two weeks to about three weeks after 100% blossom. The above method, wherein said blossom thinning composition is applied to said blossoms of fruit bearing plants when said fruit bearing plants are at about 10% blossom up to about one week after 100% blossom. The above method, wherein said blossom thinning composition is applied to said blossoms of fruit bearing plants when said fruit bearing plants are at about 10% blossom up to about 100% blossom.

The above method, wherein said blossom thinning composition is applied to said blossoms of fruit bearing plants when said fruit bearing plants are at about 50% blossom up to about two weeks to about three weeks after 100% blossom. The above method, wherein said blossom thinning composition is applied to said blossoms of fruit bearing plants when said fruit bearing plants are at about 50% blossom up to about one week after 100% blossom. The above method, wherein said blossom thinning composition is applied to said blossoms of fruit bearing plants when said fruit bearing plants are at about 50% blossom up to about 100% blossom.

A method for thinning fruit blossoms, said method comprising (or consisting essentially of or consisting of) applying to the blossoms (and associated living tissue) of fruit bearing plants a blossom thinning effective amount of eugenol and optionally a carrier or carrier material such as water.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Blossom thinning and fruit retention of peach and apple trees treated with essential oil in spring 2003.

| Concentration of active ingredient (%) | Flowers without wilted pistils and stamens 24 hr after application | | Fruit (1 to 2 cm in diameter) one month after application | | Fruit (2 to 4 cm in diameter) two months after application | |
|---|---|---|---|---|---|---|
| | Peach[a] (%) | Apple[b] (%) | Peach[a] (%) | Apple[c] (%) | Peach[a] (%) | Apple[c] (%) |
| 0 | 100 | 100 | 39 | 19 | 27 | 19 |
| 0.5 | 100 | 100 | 64 | 18 | 40 | 16 |
| 1 | 100 | 100 | 28 | 9 | 16 | 17 |
| 1.5 | 95 | 93 | 36 | 10 | 16 | 12 |
| 2 | 85 | 93 | 20 | 10 | 6 | 10 |
| 4 | 62 | 68 | 20 | 8 | 5 | 6 |
| 6 | 50 | 43 | 22 | 1 | 5 | 2 |
| 8 | 39 | 32 | 17 | 2 | 3 | 2 |
| 10 | 31 | 27 | 0 | 1 | 5 | 0 |

[a]Peach flower survival and fruit retention were counted for 100 flowers that were selected before essential oil application.
[b]Apple flower survival was counted for 100 flower clusters that were selected before essential oil application.
[c]Apple fruit retention was counted for the same 100 flower clusters that were selected before essential oil application. Each cluster contained five fruit.

TABLE 2

Flower injury in April 2004 following use of different thinning agents.

| Thinner | Rate | Flower burn back (% of flowers injured) | |
|---|---|---|---|
| | | Peach | Apple |
| Eugenol | 1% | 15 b[a] | NA |
| | 2 | 27 ab | 45 a |
| | 4 | 39 ab | 50 a |
| | 6 | NA[b] | 53 a |
| | 8 | 49 a | NA |
| Matran | 1% | 10 b | NA |
| | 2 | 19 b | 40 b |
| | 4 | 34 ab | 72 a |
| | 6 | NA | 98 a |
| | 8 | 50 a | NA |
| Wilthin | | 29 ab | NA |
| ATS | | 49 a | 50 a |
| Hand | | 6 b | NA |
| Control | | 15 b | 0 c |

[a]Means within columns followed by the same letter do not differ at P = 0.05 with Duncan's multiple range test.
[b]NA indicates that the thinner was not applied

TABLE 3

Peach and apple yields and average fruit weight from 2004 following use of different thinning agents.

| Thinner | Rate | Total yield per tree (no.) | | Average fruit weight (g) | |
|---|---|---|---|---|---|
| | | Peach | Apple | Peach | Apple |
| Eugenol | 0% | 606 ab[a] | 606 a[c] | 77 cde | 142 a |
| | 1 | 684 a | NA | 76 cde | NA |
| | 2 | 384 bc | 543 a | 87 bcde | 152 a |
| | 4 | 470 abc | 462 a | 103 abc | 155 a |
| | 6 | NA[b] | 443 a | NA | 167 a |
| | 8 | 404 bc | NA | 112 ab | NA |
| Matran | 0% | NA | 237 a | NA | 154 b |
| | 1 | 593 ab | NA | 74 cde | NA |
| | 2 | 593 ab | 210 a | 74 cde | 168 b |
| | 4 | 488 abc | 138 ab | 65 e | 219 a |
| | 6 | NA | 81 b | NA | 225 a |
| | 8 | 601 ab | NA | 69 de | NA |
| Wilthin | | 320 c | NA | 106 abc | NA |
| ATS | | 345 c | 570 a | 125 a | 153 a |
| Hand | | 347 c | NA | 98 abcd | NA |

[a]For peach, means within columns followed by the same letter do not differ at P = 0.05 with Duncan's multiple range test.
[b]NA indicates that no application of the specified thinner was made.
[c]For apple, means within columns and thinner type followed by the same letter do not differ at P = 0.05 with Duncan's multiple range test.

TABLE 4

Apple fruit response to thinning agents in 2005.

| Thinner | Eugenol conc. (%) | Fruit (no./tree) | Fruit weight (kg/tree) | Individual fruit weight (g) |
|---|---|---|---|---|
| Control | 0 | 817 a[a] | 80.8 ab | 107 d |
| ATS 2% | 0 | 789 a | 83.3 a | 109 d |
| ATS 4% | 0 | 706 ab | 79.8 ab | 120 cd |
| Matran 2% | 0.7 | 638 abc | 72.0 abc | 119 cd |
| Matran 4% | 1.4 | 460 bc | 52.7 bc | 118 cd |
| Matran 6% | 2.1 | 357 cd | 49.2 c | 139 ab |
| Eugenol 4% | 4.0 | 137 d | 20.5 d | 148 a |
| Eugenol 6% | 6.0 | 86 d | 10.2 d | 129 bc |

[a]Within a column, means followed by the same letter do not differ statistically.

We claim:

1. A method for thinning fruit blossoms, said method comprising applying an effective amount of a blossom thinning composition to the blossoms and associated living tissue of fruit bearing plants, said blossom thinning composition comprising eugenol as an active ingredient for the purpose of blossom thinning.

2. The method according to claim 1, wherein said eugenol is applied in the form of an aqueous suspension having a concentration of eugenol from about 1.5 to about 8%.

3. The method according to claim 1, wherein said eugenol is applied in the form of an aqueous suspension having a concentration of eugenol from about 1.5 to about 6%.

4. The method according to claim 1, wherein said eugenol is applied in the form of an aqueous suspension having a concentration of eugenol from about 2 to about 4%.

5. The method according to claim 1, wherein said eugenol is applied in the form of an aqueous suspension having a concentration of eugenol of about 3%.

6. The method according to claim 1, wherein said fruit bearing plants are fruit trees.

7. The method according to claim 6, wherein said fruit trees are apple trees, peach trees, or pear trees.

8. The method according to claim 6, wherein said fruit trees are apple trees.

9. The method according to claim 6, wherein said fruit trees are peach trees.

10. The method according to claim 1, wherein said blossom thinning composition is applied to said blossoms of fruit bearing plants when said fruit bearing plants are at about 10% blossom up to about two weeks to about three weeks after 100% blossom.

11. The method according to claim 1, wherein said blossom thinning composition is applied to said blossoms of fruit bearing plants when said fruit bearing plants are at about 10% blossom up to about one week after 100% blossom.

12. The method according to claim 1, wherein said blossom thinning composition is applied to said blossoms of fruit bearing plants when said fruit bearing plants are at about 10% blossom up to about 100% blossom.

13. The method according to claim 1, wherein said blossom thinning composition is applied to said blossoms of fruit bearing plants when said fruit bearing plants are at about 50% blossom up to about two weeks to about three weeks after 100% blossom.

14. The method according to claim 1, wherein said blossom thinning composition is applied to said blossoms of fruit bearing plants when said fruit bearing plants are at about 50% blossom up to about one week after 100% blossom.

15. The method according to claim 1, wherein said blossom thinning composition is applied to said blossoms of fruit bearing plants when said fruit bearing plants are at about 50% blossom up to about 100% blossom.

16. The method according to claim 1, wherein said method consists essentially of applying an effective amount of a blossom thinning composition to the blossoms and associated living tissue of fruit bearing plants, said blossom thinning composition comprising eugenol as an active ingredient for the purpose of blossom thinning.

17. A method for thinning fruit blossoms, said method comprising applying an effective amount of a blossom thinning composition to the blossoms and associated living tissue of fruit bearing plants, said blossom thinning composition comprising eugenol as an active ingredient for the purpose of blossom thinning; wherein said eugenol is applied in the form of an aqueous suspension having a concentration of eugenol from about 1.5 to about 8%.

* * * * *